United States Patent
Tsukamoto (10) Patent No.: US 10,323,241 B2
(45) Date of Patent: Jun. 18, 2019

(54) METHOD FOR RECOVERING SHORT-CHAIN NUCLEIC ACIDS

(71) Applicant: TOPPAN PRINTING CO., LTD., Tokyo (JP)

(72) Inventor: Kei Tsukamoto, Tokyo (JP)

(73) Assignee: TOPPAN PRINTING CO., LTD., Tokyo (JP)

( * ) Notice: Subject to any disclaimer, the term of this patent is extended or adjusted under 35 U.S.C. 154(b) by 239 days.

(21) Appl. No.: 15/292,880

(22) Filed: Oct. 13, 2016

(65) Prior Publication Data

US 2017/0029808 A1    Feb. 2, 2017

Related U.S. Application Data

(63) Continuation of application No. PCT/JP2015/061882, filed on Apr. 17, 2015.

(30) Foreign Application Priority Data

Apr. 18, 2014 (JP) .................. 2014-086247

(51) Int. Cl.
| | |
|---|---|
| *C07H 1/08* | (2006.01) |
| *C12Q 1/68* | (2018.01) |
| *C12N 15/10* | (2006.01) |
| *C12Q 1/6806* | (2018.01) |

(52) U.S. Cl.
CPC ........... *C12N 15/1006* (2013.01); *C07H 1/08* (2013.01); *C12Q 1/68* (2013.01); *C12Q 1/6806* (2013.01)

(58) Field of Classification Search
CPC ......... C12N 15/1006; C12Q 1/68; C07H 1/08
See application file for complete search history.

(56) References Cited

U.S. PATENT DOCUMENTS

| | | | |
|---|---|---|---|
| 5,234,809 A | 8/1993 | Boom et al. | |
| 6,180,778 B1 | 1/2001 | Bastian et al. | |
| 9,809,612 B2 * | 11/2017 | Ritt | .......................... C07H 1/08 |
| 2011/0130558 A1 | 6/2011 | Ritt et al. | |

FOREIGN PATENT DOCUMENTS

| | | |
|---|---|---|
| JP | 9-508638 | 9/1997 |
| JP | 2011-522529 | 8/2011 |
| WO | WO 93/11221 A1 | 6/1993 |
| WO | WO 2007/065934 A1 | 6/2007 |
| WO | WO 2013/037401 A1 | 3/2013 |

OTHER PUBLICATIONS

International Search Report dated Jul. 21, 2015 in corresponding International Application No. PCT/JP2015/061882.

* cited by examiner

*Primary Examiner* — Lawrence E Crane (57) ABSTRACT

A method of recovering short-chain nucleic acids having a length of 1000 bases or less from a whole blood sample, which includes bringing a first mixture including a whole blood sample into contact with a first nucleic acid adsorbent to adsorb nucleic acids derived from the whole blood sample, removing the first nucleic acid adsorbent from being in contact with the first mixture to recover liquid components of the first mixture, bringing a second mixture including the recovered liquid components into contact with a second nucleic acid adsorbent to adsorb short-chain nucleic acids having a length of 1000 bases or less from the whole blood sample, separating the second nucleic acid adsorbent from being in contact with the second mixture, and eluting the short-chain nucleic acids absorbed in the second nucleic acid adsorbent and recovering the short-chain nucleic acids from the second nucleic acid adsorbent.

12 Claims, 3 Drawing Sheets

METHOD FOR RECOVERING SHORT-CHAIN NUCLEIC ACIDS

CROSS REFERENCE TO RELATED APPLICATIONS

This application is a continuation application based on a PCT Patent Application No. PCT/JP2015/061882, filed Apr. 17, 2015, whose priority is claimed on Japanese Patent Application No. 2014-086247, filed Apr. 18, 2014, the content of which is hereby incorporated by reference.

BACKGROUND OF THE INVENTION

Field of the Invention

The present invention relates to a method for efficiently recovering nucleic acids having a relatively short chain length such as circulating DNA, from a whole blood sample containing a large amount of long-chain nucleic acids such as genomic DNA.

Description of Related Art

Currently, free nucleic acids circulating in whole blood (peripheral blood) have attracted much attention in the cancer diagnostic field. Circulating nucleic acids (DNA/RNA) in whole blood are used for various purposes, such as for diagnosing carcinomas and residual lesions associated with carcinomas, for assessing the prognosis of carcinomas, for monitoring the disease course of individuals affected by carcinomas, or for observing the effects of anti-cancer therapies on malignant tumors.

It has been reported that circulating nucleic acids (DNA/RNA) in whole blood become damaged, resulting in fragmentation thereof when the circulating nucleic acids are released into peripheral blood from the nucleus, and consequently circulate as a mono- or poly-nucleosomes (structure in which DNA is wound around a nucleosome: histone octamer) in peripheral blood. The length of circulating DNA in whole blood has been reported to vary and has been generally reported to be approximately 100 to 800 bp.

In particular, DNA in a mononucleosome has a very short chain of 148 base pairs, and is short to an extent not comparable with the chain length of blood cell-derived genomic DNA in whole blood. It has been reported to be difficult to recover mononucleosomal DNA due to such a short chain length thereof, when compared with long-chain nucleic acids.

Most of the conventional art methods for purifying nucleic acids are based on one of the following two principles. Many of the methods which have been used from long ago are methods based on a one-step method where a sample containing nucleic acids, such as a whole blood sample, is mixed with a buffer containing a chaotropic agent and an organic extractant to thereby extract nucleic acids. At least one of phenol and chloroform is mainly used as the organic extractant. Impurities such as proteins are discarded together with the organic phase, and the nucleic acids retained in the aqueous phase are isolated and recovered by a phase separation process. This method suffers from problems in that toxic and harmful organic extractants must be used and in that complicated processes are required for the purification of nucleic acids from the aqueous phase recovered by the phase separation process.

In view of the disadvantages of a one-step method, an alternative method to the one-step method has also been established. The alternative method is a method based on selective adsorption of nucleic acids onto a solid carrier (nucleic acid adsorbent) such as silicon dioxide. A sample containing nucleic acids is dissolved if necessary and then brought into contact with a nucleic acid adsorbent to thereby adsorb nucleic acids in the sample onto the nucleic acid adsorbent. The nucleic acids adsorbed onto the nucleic acid adsorbent are eluted by a suitable buffer from the nucleic acid adsorbent. A typical example of such a method may be a Boom method (see, for example, Patent Document 1 (U.S. Pat. No. 5,234,809).). The Boom method is a method in which a sample containing nucleic acids is incubated with a chaotropic buffer and a DNA-binding solid phase (nucleic acid adsorbent) to thereby isolate nucleic acids from the sample. Both extraction of nucleic acids from cells in the sample and adsorption of the extracted nucleic acids onto a nucleic acid adsorbent are realized by a chaotropic buffer. As a method similar to the above-described method, for example, Patent Document 2 (PCT International Publication No. WO 1993/11221) also discloses a method in which a sample containing nucleic acids is brought into contact with an anion exchanger in a low ionic strength buffer to adsorb nucleic acids in the sample, the nucleic acids eluted from the anion exchanger using a high ionic strength buffer are adsorbed again onto an inorganic carrier member in the presence of a lower alcohol, and then the nucleic acids are recovered by water or a low ionic strength buffer from the inorganic carrier member.

Nucleic acids having a relatively longer chain length than nucleic acids having a short chain length are readily adsorbed onto a nucleic acid adsorbent. Therefore, in the case where nucleic acids are recovered from a whole blood sample using such a method employing a nucleic acid adsorbent, blood cell-derived long chain DNA will be more preferentially recovered than circulating DNA having a short chain length, whereby it is difficult to selectively recover circulating DNA. For this reason, circulating DNA has been conventionally recovered by carrying out a nucleic acid recovery method utilizing a nucleic acid adsorbent for plasma or serum where blood cell components had been previously removed from a whole blood sample. However, there are problems that in this case a special apparatus such as a centrifuge is necessary to recover plasma or serum and the recovery method cannot be carried out if not under a well-equipped environment.

Regarding a technique for concentrating short-chain nucleic acids or a technique for separating short-chain nucleic acids from long-chain nucleic acids, for example, Patent Document 3 (Published Japanese Translation No. 2011-522529 of the PCT International Publication) discloses a method in which a sample containing nucleic acids is brought into contact with a nucleic acid adsorbent in the presence of at least one chaotropic compound and 25 to 35 volume % of at least one of a branched alcohol and an unbranched alcohol, and then the nucleic acids adsorbed onto the nucleic acid adsorbent are eluted. Further, Patent Document 4 (PCT International Publication No. WO 2007/065934) discloses a method in which short-chain nucleic acids are preferentially adsorbed onto a nucleic acid adsorbent by a combined use of citrate rather than a chaotropic salt, and an alcohol.

An object of the present invention is to provide a method of efficiently recovering short-chain DNA having a length of 1000 bases or less, such as circulating DNA, directly from a whole blood sample without requiring serum separation or plasma separation, and a kit used in the same method.

SUMMARY OF THE INVENTION

A method of recovering short-chain nucleic acids, a method for purifying short-chain nucleic acids, and a kit for recovering short-chain nucleic acids according to an aspect of the present invention are as follows.

[1] A method of recovering short-chain nucleic acids according to a first aspect of the present invention includes: a step (a) of bringing a mixture having an alcohol concentration of 0 to 5 volume %, the mixture being prepared by mixing a whole blood sample with a first buffer containing one or more members selected from the group consisting of a chaotropic agent and a surfactant, into contact with a first nucleic acid adsorbent to adsorb nucleic acids derived from the whole blood sample onto the first nucleic acid adsorbent, and then separating and removing the first nucleic acid adsorbent to recover liquid components; a step (b) of bringing a mixture having an alcohol concentration of 10 volume % or higher, the mixture being prepared by mixing the liquid components recovered in the step (a) with a second buffer containing one or more members selected from the group consisting of a chaotropic agent and a surfactant and an alcohol, into contact with a second nucleic acid adsorbent to adsorb short-chain nucleic acids having a length of 1000 bases or less derived from the whole blood sample onto the second nucleic acid adsorbent, and then separating and recovering the second nucleic acid adsorbent from the recovered liquid components; and a step (c) of eluting and recovering nucleic acids from the second nucleic acid adsorbent recovered in the step (b).

[2] A nucleic acid having a length of 5000 bases or more derived from the whole blood sample may be separated and removed by adsorbing the nucleic acid having a length of 5000 bases or more onto a nucleic acid adsorbent in the step (a).

[3] The first buffer may contain guanidine hydrochloride and a surfactant, a concentration of guanidine hydrochloride may be higher than or equal to 1 mol/L and lower than or equal to a maximum solubility, and a concentration of the surfactant may be 1 to 10 volume %.

[4] The alcohol may be isopropanol or ethanol, and an alcohol concentration in the mixture of the liquid components recovered in the step (a) and the second buffer in the step (b) may be 10 to 60 volume %.

[5] The alcohol may be isopropanol, and an isopropanol concentration in the mixture of the liquid components recovered in the step (a) and the second buffer in the step (b) may be 10 to 40 volume %.

[6] The second buffer may contain one or more chaotropic agents selected from the group consisting of guanidine thiocyanate and guanidine isothiocyanate and a surfactant, a concentration of the chaotropic agent may be higher than or equal to 0.5 mol/L and lower than or equal to a maximum solubility, and a concentration of the surfactant may be 3 to 15 volume %.

[7] The second buffer may contain 10 to 200 mmol/L of a cation salt.

[8] The step (b) may be a step (b') of adding a proteolytic enzyme to the liquid components recovered in the step (a) to carry out an enzymatic reaction, and a step (b") of bringing the mixture of the liquid components and the second buffer into contact with the second nucleic acid adsorbent to adsorb short-chain nucleic acids having a length of 1000 bases or less derived from the whole blood sample onto the second nucleic acid adsorbent, and then separating and recovering the second nucleic acid adsorbent, after the step (b').

[9] The first nucleic acid adsorbent or the second nucleic acid adsorbent may be one or more members selected from the group consisting of a silicic acid-containing material, zeolite, aluminum oxide, titanium dioxide, zirconium dioxide, kaolin, magnetic particles, ceramics, and polystyrene.

[10] The silicic acid-containing material may be silica, magnetic silica, glass, or silicon dioxide.

[11] The short-chain nucleic acid may be circulating DNA.

[12] A method of purifying short-chain nucleic acids from a whole blood sample according to a second aspect of the present invention uses the method of recovering short-chain nucleic acids according to the first aspect.

[13] A kit of recovering short-chain nucleic acids according to a third aspect of the present invention is a kit used in the method for recovering short-chain nucleic acids according to the first aspect, including: a first buffer which contains one or more members selected from the group consisting of a chaotropic agent and a surfactant, and is mixed with a whole blood sample such that an alcohol concentration is 5 volume % or lower; a second buffer which contains one or more members selected from the group consisting of a chaotropic agent and a surfactant and an alcohol, and is mixed with the liquid components from which the nucleic acid adsorbent was separated and removed after bringing the nucleic acid adsorbent into contact with the mixture of the first buffer and the whole blood sample, such that an alcohol concentration is 10 volume % or higher; and nucleic acid adsorbents.

[14] The kit for recovering short-chain nucleic acids according to the third aspect may be configured to recover circulating DNA from a whole blood sample.

According to the method of recovering short-chain nucleic acids according to the first aspect of the present invention, short-chain nucleic acids can be efficiently recovered without requiring a serum separation process or a plasma separation process from a whole blood sample where long-chain nucleic acids such as blood cell-derived genomic DNA (typically, several tens of thousands to three hundred million bp long) and short-chain nucleic acids such as circulating DNA (100 bp to 1000 bp long) are present in admixture. That is, according to the method of recovering short-chain nucleic acids according to the first aspect of the present invention, efficient purification of short-chain nucleic acids such as circulating DNA from whole blood samples can be achieved even in facilities without equipment such as a centrifuge necessary for a serum separation process or a plasma separation process.

DETAILED DESCRIPTION OF THE INVENTION

<Method for Recovering Short-Chain Nucleic Acid>

A method of recovering short-chain nucleic acids according to an embodiment of the present invention (hereinafter, sometimes referred to as "nucleic acid recovery method according to the present embodiment") is a method of recovering short-chain nucleic acids having a length of 1000 bases or less from a whole blood sample based on the principle of recovering a nucleic acid by adsorbing the nucleic acid onto a nucleic acid adsorbent, and takes advantage of the fact that the adsorbability of short-chain nucleic acids onto a nucleic acid adsorbent is strongly influenced by an alcohol concentration. The adsorbability of short-chain nucleic acids onto a nucleic acid adsorbent is very weak (low) under the environment of a low alcohol concentration or the absence of an alcohol, and is strong (high) under the high alcohol concentration environment. The adsorbability of long-chain nucleic acids onto a nucleic acid adsorbent is also affected by alcohol concentration, but the effect of the alcohol concentration is smaller than for short-chain nucleic acids. Particularly in the case of very long nucleic acids such as genomic DNA, most nucleic acids are adsorbed onto a nucleic acid adsorbent even under the environment of the absence of an alcohol. Therefore, in the nucleic acid recovery method according to the present embodiment, nucleic acids adsorbed onto a nucleic acid adsorbent are first removed from a whole blood sample under the environment of a low alcohol concentration or the absence of an alcohol, and then the remaining nucleic acids are recovered by adsorbing thereof onto the nucleic acid adsorbent under a high alcohol concentration environment.

Specifically, the nucleic acid recovery method according to the present embodiment includes the following steps (a) to (c). The mixture of a whole blood sample and a first buffer in the following step (a) does not contain an alcohol or has an alcohol concentration of 5 volume % or lower, and the alcohol concentration in the mixture of the liquid components recovered in the step (a) and a second buffer in the following step (b) is 10 volume % or higher.

The nucleic acid recovery method according to the present embodiment includes:

(1) a step (a) of bringing the mixture of a whole blood sample and a first buffer into contact with a first nucleic acid adsorbent to thereby adsorb nucleic acids derived from the whole blood sample onto the first nucleic acid adsorbent, and then separating and removing the first nucleic acid adsorbent to recover liquid components, (2) a step (b) of bringing the mixture of the liquid components recovered in the step (a) and a second buffer into contact with a second nucleic acid adsorbent to adsorb a short-chain nucleic acid having a length of 1000 bases or less derived from the whole blood sample onto the second nucleic acid adsorbent, and then separating and recovering the second nucleic acid adsorbent from the recovered liquid components, and (3) a step (c) of eluting and recovering nucleic acids from the second nucleic acid adsorbent recovered in the step (b).

In the step (a), short-chain nucleic acids are hardly adsorbed and long-chain nucleic acids such as genomic DNA are preferentially adsorbed onto the first nucleic acid adsorbent, since the alcohol concentration in the mixture of a whole blood sample and a first buffer is low at 5 volume % or lower (inclusive of 0 volume %). Therefore, by separating and removing the first nucleic acid adsorbent that has adsorbed the nucleic acids, long-chain nucleic acids are preferentially removed from whole blood sample-derived nucleic acids and consequently the abundance ratio of short-chain nucleic acids in the remaining liquid components becomes relatively high.

Then, in the step (b), the short-chain nucleic acids in the liquid components can be adsorbed onto a second nucleic acid adsorbent by bringing the recovered liquid components into contact with the second nucleic acid adsorbent in a state of making an alcohol concentration to 10 volume % or higher by mixing a second buffer into the recovered liquid components.

Then, in the step (c), nucleic acids containing short-chain nucleic acids derived from a whole blood sample can be recovered by eluting the nucleic acid from the second nucleic acid adsorbent recovered in the step (b).

With respect to adsorbability onto a nucleic acid adsorbent under the same environment, the adsorbability of long-chain nucleic acids is higher than adsorbability of short-chain nucleic acids. Therefore, in the case of being adsorbed onto a nucleic acid adsorbent in the presence of an alcohol by directly mixing a buffer containing an alcohol in a whole blood sample, short-chain nucleic acids are hardly contained in the nucleic acids recovered from the nucleic acid adsorbent, since long-chain nucleic acids are preferentially adsorbed and short-chain nucleic acids are hardly adsorbed. In contrast, in the nucleic acid recovery method according to the present embodiment, long-chain nucleic acids in the nucleic acids derived from a whole blood sample are firstly removed by adsorbing thereof onto a nucleic acid adsorbent under the environment where the adsorbability of short-chain nucleic acids is weak, and then the remaining nucleic acids not adsorbed onto the nucleic acid adsorbent are recovered by adsorbing thereof onto a fresh nucleic acid adsorbent under the environment where short-chain nucleic acids can also be adsorbed. It is possible to efficiently recover short-chain nucleic acids by adsorbing short-chain nucleic acids onto a nucleic acid adsorbent after removing most of long-chain nucleic acids from the whole blood sample-derived nucleic acids.

Although the present embodiment shows an example using two nucleic acid adsorbents, the nucleic acid recovery may be carried out by a step in which using one nucleic acid adsorbent, long-chain nucleic acids are recovered, long-chain nucleic acids adsorbed onto the nucleic acid adsorbent are eluted and the nucleic acid adsorbent is washed, and then short-chain nucleic acids are adsorbed and recovered.

The first buffer used in the present embodiment contains one or more members selected from the group consisting of a chaotropic agent and a surfactant. The chaotropic agents to be contained may be used alone or in combination of two or more thereof. Similarly, the surfactants to be contained may be used alone or in combination of two or more thereof. The first buffer is preferably a buffer containing one or two or more chaotropic agents and one or two or more surfactants.

Examples of the chaotropic agent include a guanidine salt such as guanidine hydrochloride (GHCl), guanidine thiocyanate (GTC) or guanidine isothiocyanate (GITC), sodium iodide, and sodium perchlorate. The chaotropic agent contained in the first buffer is preferably a guanidine salt and more preferably guanidine hydrochloride.

The surfactant to be used may be suitably selected from surfactants that are commonly used in the art when extracting nucleic acids from biological samples. The surfactant contained in the first buffer may be an ionic surfactant such as sodium dodecyl sulfate (SDS), but it is preferably a non-ionic surfactant, more preferably Triton (registered trademark) X (Polyoxyethylene (10) Octylphenyl Ether), Tween (registered trademark) 20 (Polyoxyethylene (20) Sorbitan Monolaurate), Tween (registered trademark) 40 (Polyoxyethylene (20) Sorbitan Monopalmitate), Tween (registered trademark) 60 (Polyoxyethylene (20) Sorbitan Monostearate), Tween (registered trademark) 80 (Polyoxyethylene (20) Sorbitan Monooleate), Nonidet (registered trademark) P-40 (Polyoxyethylene (9) Octylphenyl Ether), Brij (registered trademark) 35 (Polyoxyethylene (23) Lauryl Ether), Brij (registered trademark) 58 (Polyoxyethylene (20) Cethyl Ether), digitonin or saponin, and still more preferably Triton X, Tween 20 or Nonidet P-40.

In the case where the first buffer contains a chaotropic agent, the concentration of the chaotropic agent may be any concentration sufficient to extract nucleic acids from cells in a whole blood sample and may be appropriately adjusted in consideration of the type of chaotropic agents to be used, and whether or not chaotropic agents are used in combination with surfactants. For example, the concentration of the chaotropic agent in the first buffer is preferably higher than or equal to 1 mol/L and lower than or equal to the maximum solubility, and more preferably higher than or equal to 2 mol/L and lower than or equal to the maximum solubility.

In the case where the first buffer contains a surfactant, the concentration of the surfactant may be any concentration sufficient to extract nucleic acids from cells in a whole blood sample and may be appropriately adjusted in consideration of the type of surfactants to be used, and whether or not surfactants are used in combination with chaotropic agents. For example, the concentration of the surfactant in the first buffer is preferably 1 to 10 volume %, and more preferably 2 to 5 volume %.

The first buffer is preferably a buffer which does not contain an alcohol, but may contain an alcohol. In the case where the first buffer contains an alcohol, the alcohol concentration in the first buffer and the mixing ratio of the first buffer and the whole blood sample are appropriately adjusted such that the alcohol concentration in the mixture of the whole blood sample and the first buffer is 5 volume % or lower. By adjusting the alcohol concentration in the mixture of the whole blood sample and the first buffer to 5 volume % or lower, the amount of short-chain nucleic acids having a length of 500 bases or less adsorbed onto the first nucleic acid adsorbent separated and removed can be made less than the detection limit value. The alcohols contained in the first buffer may be used alone or in combination of two or more thereof. The alcohol to be used is preferably branched or linear alkanols having 1 to 5 carbon atoms, more preferably isopropanol or a mixed solvent of isopropanol and ethanol, and still more preferably isopropanol.

The second buffer used in the present embodiment contains one or more members selected from the group consisting of a chaotropic agent and a surfactant. The chaotropic agents to be contained may be used alone or in combination of two or more thereof. Similarly, the surfactants to be contained may be used alone or in combination of two or more thereof. The second buffer is preferably a buffer containing one or two or more chaotropic agents and one or two or more surfactants.

Examples of the chaotropic agent which may be contained in the second buffer include the same compounds as the compounds which may be contained in the first buffer. The chaotropic agent contained in the second buffer is preferably a guanidine salt, and more preferably guanidine thiocyanate or guanidine isothiocyanate exerting strong chaotropic effects even in a small amount thereof.

Examples of the surfactant which may be contained in the second buffer include the same compounds as the compounds which may be contained in the first buffer. The surfactant contained in the second buffer is preferably a non-ionic surfactant, more preferably Triton (registered trademark) X (Polyoxyethylene (10) Octylphenyl Ether), Tween (registered trademark) 20 (Polyoxyethylene (20) Sorbitan Monolaurate), Tween (registered trademark) 40 (Polyoxyethylene (20) Sorbitan Monopalmitate), Tween (registered trademark) 60 (Polyoxyethylene (20) Sorbitan Monostearate), Tween (registered trademark) 80 (Polyoxyethylene (20) Sorbitan Monooleate), Nonidet (registered trademark) P-40 (Polyoxyethylene (9) Octylphenyl Ether), Brij (registered trademark) 35 (Polyoxyethylene (23) Lauryl Ether), Brij (registered trademark) 58 (Polyoxyethylene (20) Cethyl Ether), digitonin or saponin, and still more preferably Triton X, Tween 20 or Nonidet P-40.

In the case where the second buffer contains a chaotropic agent, the concentration of the chaotropic agent may be any concentration sufficient for the nucleic acid extracted from the cells by the first buffer to maintain the extracted state and may be appropriately adjusted in consideration of the type of chaotropic agents to be used, and whether or not chaotropic agents are used in combination with surfactants. For example, the concentration of the chaotropic agent in the second buffer is preferably higher than or equal to 0.5 mol/L and lower than or equal to the maximum solubility, more preferably higher than or equal to 1 mol/L and lower than or equal to the maximum solubility, and still more preferably higher than or equal to 2 mol/L and lower than or equal to the maximum solubility.

In the case where the second buffer contains a surfactant, the concentration of the surfactant may be any concentration sufficient for the nucleic acid extracted from the cells by the first buffer to maintain the extracted state and may be appropriately adjusted in consideration of the type of surfactants to be used, and whether or not surfactants are used in combination with chaotropic agents. For example, the concentration of the surfactant in the second buffer is preferably set to 3 to 15 volume %, and more preferably set to 7 to 11 volume %.

The second buffer contains an alcohol. The alcohols contained in the second buffer may be used alone or in combination of two or more thereof. The alcohol to be used is preferably branched or linear alkanols having 1 to 5 carbon atoms commonly used in the art when extracting/purifying nucleic acids from biological samples. Examples of the alkanols include methanol, ethanol, propanol, isopropanol, butanol and pentanol. The alcohol contained in the second buffer is preferably an alcohol having a nucleic acid precipitation effect equivalent to isopropanol, more preferably ethanol, isopropanol or a mixed solvent thereof, still more preferably isopropanol or a mixed solvent of isopropanol and ethanol, and even more preferably isopropanol.

The alcohol concentration in the second buffer, and the mixing ratio of the liquid components recovered in the step (a) and the second buffer are appropriately adjusted such that the alcohol concentration in the mixture of the liquid components and the second buffer is 10 volume % or higher. In the case where the alcohol contained in the second buffer is isopropanol, the isopropanol concentration in the second buffer and the mixing ratio of the liquid components and the second buffer are preferably adjusted such that the isopropanol concentration in the mixture of the liquid components and the second buffer is 10 to 40 volume %. In the case where the alcohol contained in the second buffer is ethanol, the ethanol concentration in the second buffer and the mixing ratio of the liquid components and the second buffer are preferably adjusted such that the ethanol concentration in the mixture of the liquid components and the second buffer is 30 to 60 volume %.

The second buffer used in the present embodiment also preferably further contains a cation salt. The cation salt may be a monovalent cation salt or a divalent cation salt. Examples of the cation constituting the cation salt include a lithium ion, a sodium ion, a potassium ion, a rubidium ion, a cesium ion, an ammonium ion, a magnesium ion, a calcium ion, and a strontium ion. The cation constituting the cation salt is preferably a lithium ion, a sodium ion, a magnesium ion, or a calcium ion. The anion constituting the anion salt is preferably a chloride ion, a bromide ion or an iodide ion, more preferably a chloride ion or a bromide ion, and still more preferably a chloride ion.

In the case where the second buffer contains a cation salt, the cation salt concentration in the second buffer may be any concentration at which extraction/purification of nucleic acids is possible from a biological sample by an alcohol precipitation method, and is appropriately determined in consideration of the type of cation salts to be used. With respect to the second buffer used in the present embodiment, 10 to 200 mmol/L is preferable taking into consideration that the recovered short-chain nucleic acid is subjected to a commonly used analysis such as PCR.

The first buffer is prepared by dissolving at least one of a chaotropic salt and a surfactant, and if necessary, an alcohol and other ingredients in water or a buffer. The second buffer is prepared by dissolving at least one of a chaotropic salt and a surfactant and an alcohol, and if necessary, a cation salt and other ingredients in water or a buffer. In the case where the solvent for preparing the first buffer and the second buffer is a buffer, a pH of the buffer is suitably determined in consideration of the type of the nucleic acid to be extracted (DNA or RNA), the analysis method where the recovered nucleic acid is used, and the like. In the present embodiment, a pH value of the first buffer and the second buffer is preferably pH 5 to 9, and more preferably pH 6.5 to 8.5. In the case where the nucleic acid to be extracted is DNA, a pH of 7.0 to 8.5 is particularly preferable. The buffer serving as the solvent for preparing the first buffer and the second buffer may be appropriately selected from the buffers commonly used in the art at the time of extraction, purification and analysis of nucleic acids. Specific examples of the buffer include a Tris (trishydroxymethylaminomethane)-HCl buffer, and a phosphate buffer. The water serving as the solvent for preparing the first buffer and the second buffer is preferably deionized water or ultrapure water.

Further, the first buffer and the second buffer may contain other substances other than chaotropic agents, surfactants, alcohols and cation salts, as long as they do not inhibit the effect of the present embodiment.

The first nucleic acid adsorbent and the second nucleic acid adsorbent used in the present embodiment are not particularly limited as long as they are a solid capable of adsorbing nucleic acids. The material for the nucleic acid adsorbent is preferably one or more members selected from the group consisting of a silicic acid-containing material such as silica, magnetic silica, glass or silicon dioxide, zeolite, aluminum oxide, titanium dioxide, zirconium dioxide, kaolin, magnetic particles, ceramics and polystyrene, and more preferably a silicic acid-containing material. Among them, it is more preferable to use a silica membrane, silica gel, magnetic particles having silica or glass on the surface thereof, or a combination of these materials. The first nucleic acid adsorbent and the second nucleic acid adsorbent may employ a material of the same type.

The shape of the first nucleic acid adsorbent and the second nucleic acid adsorbent is not particularly limited and may be of a particulate shape, a membrane shape, or a shape fixed to the inner wall surface of a container or the like.

Hereinafter, individual steps will be described.

First, in the step (a), a mixture of a whole blood sample and a first buffer is brought into contact with a first nucleic acid adsorbent. In the mixture of the whole blood sample and the first buffer, nucleic acids are extracted from the cells in the whole blood sample by the chaotropic agent or the surfactant derived from the first buffer.

By bringing the mixture into contact with the first nucleic acid adsorbent, the extracted nucleic acids are adsorbed onto the nucleic acid adsorbent. For example, in the case where the first nucleic acid adsorbent is of a particulate shape, the mixture of the whole blood sample and the first buffer can be brought into contact with the nucleic acid adsorbent by adding the nucleic acid adsorbent to the mixture. In the case where the first nucleic acid adsorbent is fixed to the inner wall surface of a container or the like, the mixture can be brought into contact with the nucleic acid adsorbent by mixing the whole blood sample and the first buffer in the container, or by placing the mixture of the whole blood sample and the first buffer in the container.

The whole blood sample-derived nucleic acids are adsorbed onto a first nucleic acid adsorbent and then the first nucleic acid adsorbent is separated and removed to recover liquid components. Separation and removal of the first nucleic acid adsorbent and recovery of the liquid components can be carried out by a widely used solid-liquid separation operation. For example, in the case where the first nucleic acid adsorbent is granular, only the liquid components can be recovered by centrifuging a solution containing the first nucleic acid adsorbent (a mixture of the whole blood sample, the first buffer and the first nucleic acid adsorbent) to precipitate the nucleic acid adsorbent, and then collecting the supernatant. Further, only the liquid components passed through a porous membrane or a filter paper can also be recovered by passing a solution containing the first nucleic acid adsorbent through a porous membrane or filter paper having a small pore diameter to such an extent that the nucleic acid adsorbent cannot permeate. Additionally, in the case where the first nucleic acid adsorbent is magnetic particles, only the liquid components can be recovered by using a magnet. In the case where the first nucleic acid adsorbent is membrane-like such as a silica membrane, only the liquid components can be recovered by permeating a mixture of the whole blood sample and the first buffer through a silica membrane to thereby bring the mixture into contact with the nucleic acid adsorbent. When the mixture is passed through a silica membrane, a liquid may be removed from the silica membrane by subjecting it to centrifugation, vacuum or pressurization.

A first nucleic acid adsorbent may be mixed with a whole blood sample simultaneously with mixing of the whole blood sample with a first buffer. Alternatively, the first nucleic acid adsorbent may be brought into contact with the mixture after sufficient extraction of nucleic acids from cells in the whole blood sample by incubating the mixture of the whole blood sample and the first buffer for a certain period of time. Alternatively, liquid components may be immediately recovered by bring the first nucleic acid adsorbent into contact with the mixture of the whole blood sample and the first buffer. Alternatively, the first nucleic acid adsorbent may be separated and removed after incubating the mixture of the whole blood sample and the first buffer for a certain period of time in a state of being in contact with the first nucleic acid adsorbent.

In the step (a), the amount of the first nucleic acid adsorbent to be used, and the time conditions until separating and removing the nucleic acid adsorbent from the time of bringing the first nucleic acid adsorbent into contact with the mixture of the whole blood sample and the first buffer are preferably adjusted such that almost all of the genomic DNA derived from the whole blood sample is adsorbed onto the first nucleic acid adsorbent, and the amount of the nucleic acid having a length of several tens of thousand bases or more adsorbed onto the second nucleic acid adsorbent in the step (b) is less than the detection limit value. Further, it is more preferable to adjust such that almost all of the nucleic acid having a length of 5000 bases or more derived from the whole blood sample are adsorbed onto the first nucleic acid adsorbent, and the amount of the nucleic acid having a length of 5000 bases or more adsorbed onto the second nucleic acid adsorbent in the step (b) is less than the detection limit value. By removing a long-chain nucleic acid by sufficiently adsorbing thereof onto the first nucleic acid adsorbent in the step (a), it is possible to selectively recover a desired short-chain nucleic acid.

The first buffer may contain a proteolytic enzyme. Use of a proteolytic enzyme enables to more efficiently carry out the extraction of nucleic acids from cells in a whole blood sample. Examples of the proteolytic enzyme include lysozyme, proteinase, proteinase K, and cellulase. In the case where the first buffer contains a proteolytic enzyme, it is preferable to carry out an enzymatic reaction by incubating the mixture of a whole blood sample and a first buffer for approximately 5 minutes to 2 hours in a temperature range where the contained proteolytic enzyme may exert enzymatic activity, preferably in the vicinity of an optimum temperature for the enzymatic activity of the proteolytic enzyme.

The enzymatic reaction may be carried out prior to bringing a first nucleic acid adsorbent into contact with the mixture of the whole blood sample and the first buffer, or may be carried out after contacting therebetween and prior to separation and removal of the first nucleic acid adsorbent. Further, the incubation for the enzymatic reaction may also serve as the incubation for adsorption of the extracted nucleic acid onto the first nucleic acid adsorbent.

Then, as the step (b), the mixture of the liquid components recovered in the step (a) and the second buffer is brought into contact with a second nucleic acid adsorbent to thereby adsorb short-chain nucleic acids having a length of 1000 bases or less derived from the whole blood sample onto the second nucleic acid adsorbent, and then the second nucleic acid adsorbent is separated and recovered from the liquid components. The method of bringing the mixture of the liquid components recovered in the step (a) and the second buffer into contact with the second nucleic acid adsorbent, or the method of adsorbing the nucleic acid in the liquid components onto the second nucleic acid adsorbent may be carried out in the same manner as in the method of bringing the mixture of a whole blood sample and a first buffer into contact with a first nucleic acid adsorbent in the step (a), or the method of adsorbing a nucleic acid derived from a whole blood sample onto a first nucleic acid adsorbent. Further, the method of separating and recovering a second nucleic acid adsorbent may be carried out in the same manner as in the separation and removal of a first nucleic acid adsorbent.

In the case where a proteolytic enzyme was not contained in the first buffer, it is also preferable to carry out a proteolytic enzyme reaction prior to separating and recovering a second nucleic acid adsorbent. The proteolytic enzyme to be used may be the same material as the material that may be contained in the first buffer. For example, it is preferable to carry out an enzymatic reaction by containing a proteolytic enzyme in the second buffer and incubating a mixture of the liquid components recovered in (a) and a second buffer for approximately 5 minutes to 2 hours in a temperature range where the contained proteolytic enzyme can exert an enzymatic activity, preferably in the vicinity of an optimum temperature for the enzymatic activity of the proteolytic enzyme.

In the case where carrying out a proteolytic enzyme reaction in the step (b), it is also preferable to carry out the proteolytic enzyme reaction prior to bringing into contact with the second nucleic acid adsorbent. Specifically, the step (b) is changed to the following steps (b') and (b"). In the step (b"), the alcohol concentration in the mixture of the liquid components and the second buffer after the enzymatic reaction is 10 volume % or higher.

(1) a step (b') of adding a proteolytic enzyme to the liquid components recovered in the step (a) to carry out an enzymatic reaction, and (2) a step (b") of bringing the mixture of the liquid components and a second buffer into contact with a second nucleic acid adsorbent to adsorb short-chain nucleic acids having a length of 1000 bases or less derived from the whole blood sample onto the second nucleic acid adsorbent, and then separating and recovering the second nucleic acid adsorbent, after the step (b').

In the step (b'), a chaotropic agent or a surfactant may be newly added together with a proteolytic enzyme. The chaotropic agent and the surfactant may employ the same material as the material exemplified as a material which may be contained in a second buffer. In the case where the reaction solution of the proteolytic enzyme reaction in the step (b') contains a chaotropic agent, the concentration of the chaotropic agent in the reaction solution is preferably 0.5 to 2.5 mol/L. In the case where the reaction solution of the proteolytic enzyme reaction in the step (b') contains a surfactant, the concentration of the surfactant in the reaction solution is preferably 3 to 15 volume %, and more preferably 7 to 11 volume %.

In the step (b'), a cation salt may be newly added together with a proteolytic enzyme. The cation salt may employ the same material as the material exemplified as a material which may be contained in a second buffer. In the case where the reaction solution of the proteolytic enzyme reaction in the step (b') contains a cation salt, the concentration of the cation salt in the reaction solution is preferably 10 to 200 mmol/L.

Then, as the step (c), the nucleic acid is eluted and recovered from the second nucleic acid adsorbent recovered in the step (b). The elution and recovery of the nucleic acid from the second nucleic acid adsorbent may be carried out by a method which has been commonly carried out when eluting the nucleic acid adsorbed onto silica or the like. For example, water may be used as an eluting solution. Specifically, by bringing water into contact with a second nucleic acid adsorbent, it is possible to elute the nucleic acid adsorbed to the second nucleic acid adsorbent.

The second nucleic acid adsorbent recovered in the step (b) may be washed with a suitable solution, prior to the step (c). From the viewpoint of no possibility of the nucleic acid being desorbed from the nucleic acid adsorbent and also no incorporation of new salts or the like, the washing solution is preferably 70 to 95 volume % of an aqueous alcohol solution, and more preferably 70 to 95 volume % of an aqueous ethanol solution.

The whole blood sample subjected to the nucleic acid recovery method according to the present embodiment may be a sample containing blood cells and plasma components. As the whole blood sample subjected to the nucleic acid recovery method according to the present embodiment, it is preferable to use whole blood collected from an animal such as human or mouse as it is as a sample, but a sample subjected to a process that can leave at least a portion of blood cell components and plasma components in whole blood may be subjected to the step (a) as a whole blood sample. An example of such a process may be a filtration process which carries out size separation to remove or recover only blood cell components of a particular size, or specific adsorption separation to remove or recover only blood cell components presenting a specific surface antigen.

The nucleic acid recovered in the nucleic acid recovery method according to the present embodiment may be DNA or RNA. Further, the nucleic acid may be a single-stranded nucleic acid or a double-stranded nucleic acid and may be a linear nucleic acid or a circular nucleic acid such as a plasmid. Further, the nucleic acid may be an epigenetically modified nucleic acid. Further, the nucleic acid may be a nucleic acid contained in a whole blood sample, and the nucleic acid may be a cell nucleus-derived nucleic acid of cells of the organism species from which blood has been collected, a mitochondria-derived nucleic acid, a nucleic acid derived from a microorganism incorporated into such a blood-collected organism, or an artificial or synthetic nucleic acid. Examples of the artificial or synthetic nucleic acid include cosmids, vectors, cDNAs, and fragments thereof.

The nucleic acid recovery method according to the present embodiment can efficiently recover short-chain nucleic acids having a length of 1000 bases or less.

With respect to the nucleic acid recovery method according to the present embodiment, a desired nucleic acid to be recovered is preferably a short-chain nucleic acid having a length of 800 bases or less, more preferably a short-chain nucleic acid having a length of 500 bases or less, or still more preferably a short-chain nucleic acid having a length of 200 bases or less. The nucleic acid recovery method according to the present embodiment is suitable for concentrating and purifying circulating DNAs in whole blood, non-coding RNAs, miRNAs, short-chain synthetic nucleic acids, and the like.

The nucleic acid recovery method according to the present embodiment is particularly suitable for purifying circulating DNAs in whole blood. In a conventional method, tumor-derived nucleic acids freely circulating in peripheral blood have been purified and recovered from the serum or plasma, whereas in the nucleic acid recovery method according to the present embodiment, freely circulating tumor-derived nucleic acids can be purified directly from a whole blood sample, taking advantage of the selectivity of a nucleic acid to be adsorbed onto a nucleic acid adsorbent. In addition, the nucleic acid recovery method according to the present embodiment can also be automated, since the operation of individual steps is relatively simple. Further, circulating DNAs recovered by the nucleic acid recovery method according to the present embodiment can be suitably subjected to a variety of analysis methods, since those circulating DNAs recovered have been purified so as to remove long-chain nucleic acids such as genomic DNA. That is, the nucleic acid recovery method according to the present embodiment is a method that can be developable in the clinical research and diagnostic field by combining various analysis methods.

The short-chain nucleic acid obtained by the nucleic acid recovery method according to the present embodiment may be subjected to any nucleic acid analysis, but it is preferable to be subjected to the analysis of particularly gene polymorphism and gene mutation (genetic test or the like) and it is more preferable to be subjected to the analysis of SNP (single nucleotide polymorphism) and single gene mutation. In particular, in the case where circulating DNA derived from cancer cells is intended to be a short-chain nucleic acid to be recovered, the recovered circulating DNA is subjected to a nucleic acid analysis for various purposes, such as for assessing the prognosis of carcinomas, for monitoring the disease course of individuals affected by carcinomas, or for observing the effects of anti-cancer therapies on malignant tumors.

Nucleic acid analysis including gene analysis usually analyzes a nucleic acid to be analyzed, and interprets the information obtained as a result of the analysis. The nucleic acid analysis is primarily carried out by a method of directly reading the base sequence of a nucleic acid by using a sequencer or the like, a method using a polymerase reaction starting from a primer that specifically hybridizes to the region consisting of a specific base sequence, or a method using a probe that specifically hybridizes to the region consisting of a specific base sequence. Since the short-chain nucleic acids obtained by the nucleic acid recovery method according to the present embodiment usually contain nucleic acids of a wide variety of genes or fragments thereof, it is preferable that the analysis target gene be analyzed by a method using at least one of a primer and a probe. Examples of the method using at least a primer include a PCR (polymerase chain reaction) method, a real-time PCR method, a TaqMan (registered trademark)-PCR method, a LAMP (Loop-Mediated Isothermal Amplification) method, a SMAP (SMart Amplification Process) method, a NASBA (Nucleic Acid Sequence-Based Amplification) method, an RCA (rolling circle amplification) method, and modified methods thereof. Examples of the method using a probe include an Invader (registered trademark) method, and a DNA microarray. These methods may be used in combination as appropriate.

In the nucleic acid recovery method according to the present embodiment, there is a case where merely a trace amount of short-chain nucleic acids is obtained. Therefore, the method for analyzing short-chain nucleic acids recovered by the nucleic acid recovery method according to the present embodiment is preferably (1) an analysis method utilizing a nucleic acid amplification reaction using a probe, (2) a method including a first step of amplifying a nucleic acid by PCR or the like, and a second step of carrying out a nucleic acid analysis for the amplification product obtained in the first step. The above-mentioned method (1) may include, for example, an allele-specific extension method for carrying out an extension reaction using a primer specific for a particular genotype, and TaqMan-PCR method. The above-mentioned method (2) may include, for example, an Invader Plus method, a restriction fragment length polymorphism (PCR-RFLP) method, and a single strand conformation polymorphism (PCR-SSCP) method. Among them, an Invader Plus method is preferable, in which the short-chain nucleic acid obtained by the nucleic acid recovery method according to the present embodiment is first amplified by PCR, and then an Invader method is carried out on the obtained amplification product because it is possible to carry out a nucleic acid analysis with high sensitivity and high accuracy even in the case where the short-chain nucleic acid to be analyzed is present in a very small amount. Further, it is also possible to employ a nucleic acid analysis method that does not require nucleic acid amplification steps such as PCR.

Hereinafter, an example of a method to detect and analyze a particular gene (gene to be analyzed) by an Invader Plus method is shown, but the nucleic acid analysis method of short-chain nucleic acids recovered by the nucleic acid recovery method according to the present embodiment is not limited thereto.

First, an Invader Plus buffer which is an Invader Plus reaction solution, an oligo mix for detecting a gene to be analyzed, and an enzyme mix were mixed in the short-chain nucleic acid solution recovered by the nucleic acid recovery method according to the present embodiment (in the step (c), an eluate in which nucleic acids were eluted from a second nucleic acid adsorbent), followed by denaturation (heating at 95° C. for 2 minutes) to melt double helix of DNA into single strands. The oligo mix includes PCR primers, DNA probes, invading oligos, and a FRET cassette.

Then, PCR is carried out, resulting in an amplification reaction of a nucleic acid of a portion corresponding to the gene to be analyzed, and then deactivation of polymerase is carried out to stop PCR.

Finally, an Invader (registered trademark) method is carried out to degrade a DNA probe which has specifically hybridized to the region having a nucleic acid sequence corresponding to the gene to be analyzed. Then, the 5'-oligonucleotide of the heated probe of DNA produced by the decomposition reaction is combined with an FRET cassette having a fluorescent dye. The FRET cassette is degraded and a fluorescent dye is liberated from the FRET cassette, resulting in emission of fluorescence. The gene to be analyzed can be indirectly detected and measured by measuring this fluorescence. In other words, the fluorescence signal intensity indicates a detected amount of the corresponding gene to be analyzed.

The fluorescent signal intensity of a fluorescent dye dissociated by an Invader (registered trademark) method (for example, the fluorescent signal intensity (excitation wavelength: 485 nm, and emission wavelength: 535 nm) of FAM in the case where the fluorescent dye is FAM) is measured using a fluorometer. The fluorometer may be, for example, a fluorometer LightCycler480 manufactured by Roche Applied Science.

<Kit of Recovering Short-Chain Nucleic Acid>

The nucleic acid recovery method according to a second embodiment of the present invention can be more conveniently carried out by fabricating reagents used, and the like into a kit. The kit for carrying out the nucleic acid recovery method according to the present embodiment preferably contains the first buffer, the second buffer, and nucleic acid adsorbent used as the first nucleic acid adsorbent and the second nucleic acid adsorbent. The first buffer is a buffer which is mixed with a whole blood sample such that the alcohol concentration in the mixture is 5 volume % or lower. The second buffer is a buffer which is mixed in the liquid components obtained by bringing a nucleic acid adsorbent into contact with the mixture of the first buffer and the whole blood sample, and then separating and removing the nucleic acid adsorbent, such that the alcohol concentration in the mixture is 10 volume % or higher. Additionally, the kit may contain a proteolytic enzyme for adding to a first buffer or the like, a washing solution for washing a second nucleic acid adsorbent onto which nucleic acids are adsorbed, an eluate for eluting nucleic acids from a second nucleic acid adsorbent onto which nucleic acids are adsorbed, or the like, if necessary.

EXAMPLES

Hereinafter, the present invention will be described in detail with reference to the following examples, but the present invention is not limited thereto.

Reference Example 1 dsDNA fragment standard samples of 200 bp, 500 bp and 1000 bp (manufactured by Gensura Laboratories), and a human genomic DNA (manufactured by GEN Script) were examined for the adsorbability thereof to a silica membrane filter (corresponding to a nucleic acid adsorbent) in a state of those samples being dissolved in buffer 1(3 mol/L of guanidine hydrochloride, and 10 volume % of Triton X) or buffer 2 (1.2 mol/L of guanidine thiocyanate, 10 volume % of Tween20, 40 volume % of isopropanol, and 100 mmol/L of $MgCl_2$). Note that buffer 1 corresponds to a first buffer used in the nucleic acid recovery method according to a first embodiment of the present invention, and buffer 2 corresponds to a second buffer used in the nucleic acid recovery method according to the present embodiment.

Specifically, a DNA solution obtained by dissolving 1000 ng of DNA in buffer 1 or buffer 2 was passed through a silica membrane filter to thereby adsorb the DNA onto the silica membrane filter. Then, purified water was passed through the silica membrane filter to elute the DNA from the silica membrane filter.

The DNA concentration in the resulting eluate was measured using a PicoGreen reagent (Invitrogen) to calculate the total amount of DNA in the eluate (recovered amount of DNA). The total amount of DNA in the eluate corresponds to an amount adsorbed onto the silica membrane filter. From the calculated total DNA amount in the eluate and the total DNA amount in the DNA solution (1000 ng) which had been passed through a silica membrane filter, the DNA recovery rate (%) using a silica membrane filter was calculated (calculation equation: [Total DNA amount in eluate (ng)]/[1000 (ng)]×100). The calculated recovery rate is shown in Table 1.

TABLE 1

| | DNA recovery | |
|---|---|---|
| DNA length | Buffer 1 | Buffer 2 |
| 200 bp | 6.5% | 89.8% |
| 500 bp | 6.2% | 84.4% |
| 1000 bp | 29.4% | 89.3% |
| Genomic DNA | 85.1% | 91.8% |

As shown in Table 1, in the case of DNA dissolved in buffer 2 where an isopropyl alcohol concentration is 40 volume %, the DNA recovery rate was very high at 80% or higher regardless of the DNA length. The DNA recovery rate in the case of DNA dissolved in buffer 1 containing no alcohol was high at 80% or higher in genomic DNA, but it was merely approximately 30% in dsDNA (double-stranded DNA) of 1000 bp, very low with less than 10% in dsDNA of 500 bp and 200 bp, and short-chain nucleic acids of 1000 bp or less were found to exhibit almost no adsorption onto a silica membrane filter. From these results, it was found that short-chain nucleic acids of 1000 bp or less are hardly adsorbed and long-chain nucleic acids such as blood cell-derived genomic DNA are preferentially adsorbed in the absence of an alcohol when adsorbing nucleic acids onto a nucleic acid adsorbent. Further, from these results, it was found that under the environment where an isopropanol concentration is 40 volume %, short-chain nucleic acids of 1000 bp or less, particularly 800 bp or less are also strongly adsorbed onto a nucleic acid adsorbent and then can be recovered. From these results, it has been suggested that short-chain nucleic acids of 1000 bp or less including circulating DNA, particularly short-chain nucleic acids of 800 bp or less can be recovered by first adsorbing whole blood sample-derived nucleic acids onto a nucleic acid adsorbent in the absence of an alcohol to be able to selectively remove long-chain nucleic acids while leaving short-chain nucleic acids of 1000 bp or less in liquid components, and then by bringing a fresh nucleic acid adsorbent into contact with the remaining liquid components freed of the nucleic acid adsorbent in the presence of a high-concentration alcohol to thereby adsorb nucleic acids.

The pH of each buffer in the embodiment of the present invention was between 7.5 and 8.0.

Reference Example 2

Commercially available human plasma and human serum (both manufactured by Lonza) were subjected to an enzymatic treatment with a proteolytic enzyme, and then short-chain nucleic acids were recovered. Proteinase K (Merck) was used as a proteolytic enzyme.

Specifically, first, 500 μL of proteinase K and 5 mL of buffer 3 (2.0 mol/L of guanidine thiocyanate, and 15 volume % of Tween20) were added to 5 mL of human plasma or human serum, followed by mixing to prepare an enzymatic reaction solution. The resulting enzymatic reaction solution was incubated at 52° C. for 30 minutes to carry out an enzymatic reaction, followed by heating at 70° C. for 10 minutes to inactivate proteinase K.

Then, 10 mL of buffer 4 (1.5 mol/L of guanidine thiocyanate, 10 volume % of Tween20, 40 volume % of isopropanol, and 100 mmol/L of $MgCl_2$) was added to the post-inactivation reaction solution, followed by mixing. Note that buffer 4 corresponds to the second buffer used in the nucleic acid recovery method according to a first embodiment of the present invention, and the alcohol concentration of the resulting mixture was approximately 20 volume %. The mixture was passed through a silica membrane filter to adsorb DNA on the silica membrane filter. Thereafter, a 70 mass % aqueous ethanol solution was permeated through the silica membrane filter to wash the filter, and then purified water was passed to elute the DNA from the silica membrane filter.

The amount of DNA in the resulting eluate (recovered amount of DNA) was determined in the same manner as in Reference Example 1, and the recovered amount of DNA per 1 mL of human plasma or human serum (DNA recovery amount per 1 mL of a sample (ng/sample 1 mL)) was calculated. Further, the ratio of absorbance at 260 nm (A260) vs. absorbance at 280 nm (A280) of the eluate ([A260]/[A280]) was determined in order to examine the purity of recovered DNA.

As a control, nucleic acids were purified from the same amount of human plasma or human serum as in the method using buffers 3 and 4 (hereinafter, referred to as "step (b')+(b") variant"), using a commercially available nucleic acid purification kit QIAamp Circulating Nucleic Acid Kit (manufactured by Qiagen) according to the instructions attached to the kit. The amount of DNA in the recovered DNA solution (recovered amount of DNA), the DNA recovery amount per 1 mL of human plasma or human serum (ng/sample 1 mL), and the purity of DNA ([A260]/[A280]) were determined in the same manner as in the eluate recovered in the step (b')+(b") variant.

Each measurement was carried out independently in triplicate, and an average and standard deviation were determined. The results are shown in Table 2. Consequently, in the case where nucleic acids were recovered from human plasma, the recovery amount of DNA and the purity of recovered DNA were both comparable in the step (b')+(b") variant and the method using a commercially available nucleic acid purification kit. In addition, in the case where nucleic acids were recovered from human serum, the step (b')+(b") variant was able to recover a high-purity DNA comparable to that of the method using a commercially available nucleic acid purification kit in a larger amount than the method using a commercially available nucleic acid purification kit.

TABLE 2

| DNA sample | Recovery method | Recovered amount of DNA(ng) Average | S.D. | Purity of DNA (A260/A280) Average | S.D. | Recovered amount of DNA per 1 mL of sample (ng/ sample 1 mL) Average |
|---|---|---|---|---|---|---|
| Human plasma | Step (b') + (b") variant | 66.5 | 1.8 | 0.9 | 0.2 | 133 |
| | Commercially available nucleic acid purification kit | 63.5 | 2.2 | 1.0 | 0.1 | 127 |
| Human serum | Step (b') + (b") variant | 103.1 | 11.6 | 1.1 | 0.0 | 206 |
| | Commercially available nucleic acid | 61.4 | 11.7 | 0.9 | 0.0 | 123 |

Reference Example 3

Nucleic acids in the human whole blood were recovered using a first buffer and a silica membrane filter (nucleic acid adsorbent) used in the nucleic acid recovery method according to a first embodiment of the present invention. Buffer 1 used in Reference Example 1 was employed as the first buffer.

Specifically, a mixture of 100 μL of human whole blood and 500 μL of buffer 1 was passed through a silica membrane filter to adsorb human whole blood-derived nucleic acids onto the silica membrane filter. Then, a 70 (mass/volume)% aqueous ethanol solution was permeated through the silica membrane filter to wash the filter, and purified water was passed to elute nucleic acids from the silica membrane filter.

Figure 1:
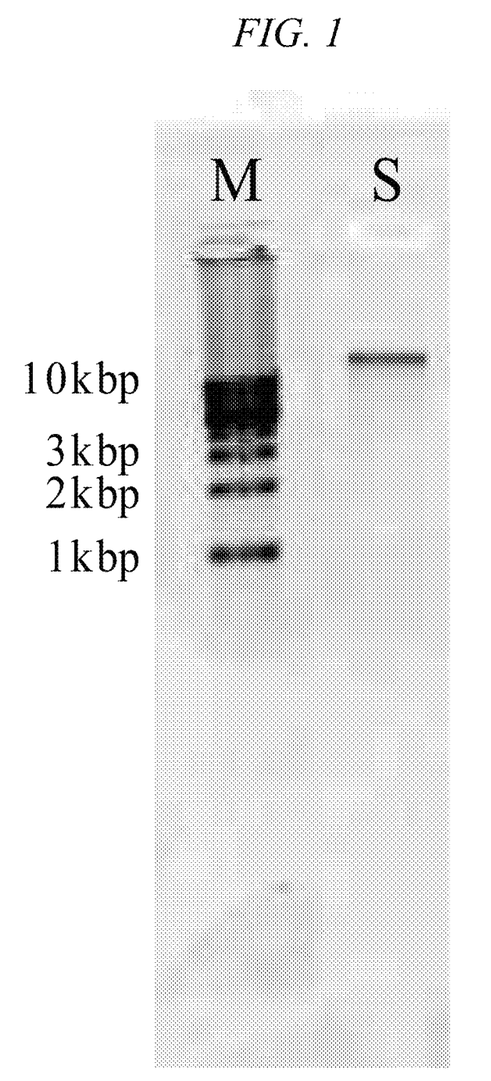
FIG. 1 is a view showing the results of agarose electrophoresis of the recovered eluate in Reference Example 3.

The chain length of DNA contained in the resulting eluate was confirmed by agarose electrophoresis. FIG. 1 shows the electrophoresis results. Referring to FIG. 1, the left lane (M) is the electrophoresis results of a 1 kbp Ladder DNA marker, and the right lane (S) is the electrophoresis results of the eluate. As shown in FIG. 1, the eluate contained merely DNA of a long chain length, and particularly a band smaller than a 1 kbp marker was not observed at all. From these results, it was demonstrated that long-chain nucleic acids are selectively adsorbed and short-chain nucleic acids are not adsorbed in the case where nucleic acids are adsorbed by a nucleic acid adsorbent from the mixture of the first buffer and the whole blood sample used in the nucleic acid recovery method according to the present embodiment. That is, it was found that there is no risk of unintentional recovery of short-chain nucleic acids including circular DNA in the step (a) of the nucleic acid recovery method according to the present embodiment.

Reference Example 4

The effect of alcohol concentration on the strength of DNA of 200 bp, 500 bp or 1000 bp to adsorb onto a nucleic acid adsorbent was examined. dsDNA fragment standard samples of 200bp, 500 bp and 1000 bp used in Reference Example 1 were employed as the dsDNA. In addition, alcohol-free buffer 4-1 (3 mol/L of guanidine hydrochloride, and 10 volume % of Triton X), 5volume % alcohol-containing buffer 4-2 (3 mol/L of guanidine hydrochloride, 10 volume % of Triton X, and 5 volume % of isopropanol), and 10 volume % alcohol-containing buffer 3 (3 mol/L of guanidine hydrochloride, 10 volume % of Triton X, and 10 volume % of isopropanol) were used as a buffer for dissolving DNA.

Specifically, a DNA solution where 1000 ng of DNA had been dissolved in buffer 4-1, 4-2 or 4-3 was passed through a silica membrane filter to adsorb the DNA onto the silica membrane filter. Then, purified water was passed through the silica membrane filter to elute the DNA from the silica membrane filter.

The total amount of DNA in the resulting eluate (recovered amount of DNA) and the DNA recovery rate (%) were determined in the same manner as in Reference Example 1. The results are shown in Table 3. Consequently, DNA of 200 bp and 500 bp could hardly be recovered in the case of using buffer 4-2 where the isopropanol concentration is 5 volume %, similar to the case of using buffer 4-1 where the isopropanol concentration is 0 volume %. To the contrary, in the case of using buffer 4-3 where the isopropanol concentration is 10 volume %, the recovery rate of DNA of 200 bp have remarkably increased by 20% or higher, and the recovery rate of DNA of 500 bp have remarkably increased by 50% or higher. Based on these results, it has been suggested that the loss of short-chain nucleic acids can be inhibited by adjusting the alcohol concentration in the mixture of a first buffer and a whole blood sample to be 5 volume % or lower, in the case where the first buffer contains an alcohol in the nucleic acid recovery method according to a first embodiment of the present invention.

TABLE 3

| | DNA recovery | | |
|---|---|---|---|
| DNA length | Buffer 4-1 (Alcohol 0 volume %) | Buffer 4-2 (Alcohol 5 volume %) | Buffer 4-3 (Alcohol 10 volume %) |
| 200 bp | 6.5% | 8.9% | 20.5% |
| 500 bp | 6.2% | 10.3% | 58.3% |
| 1000 bp | 29.4% | 34.0% | 75.2% |

Example 1

A short-chain nucleic acid was recovered from a human whole blood sample by the nucleic acid recovery method according to a first embodiment of the present invention. In addition, from the human serum sample which was prepared the same donor-derived human whole blood having an equal volume of the nucleic acid-recovered human whole blood sample, short-chain nucleic acids were recovered by the steps (b) and (c) in the nucleic acid recovery method according to the present embodiment.

For recovering nucleic acids from a human whole blood sample, specifically, 1 mL of a human whole blood sample and 5 mL of buffer 1 used in Reference Example 1 were mixed, and the prepared mixture was passed through a silica membrane filter. 600 µL of proteinase K and 6 mL of buffer 3 used in Reference Example 2 were added to 5 mL of the solution (liquid components) permeated through the silica membrane filter, followed by mixing to prepare an enzymatic reaction solution. The resulting enzymatic reaction solution was incubated at 52° C. for 30 minutes to carry out an enzymatic reaction, followed by heating at 70° C. for 10 minutes to inactivate proteinase K.

Then, 12 mL of buffer 4 used in Reference Example 2 was added to the post-inactivation reaction solution, followed by mixing. The alcohol concentration of the resulting mixture was approximately 20 volume %. The mixture was passed through a silica membrane filter to adsorb DNA on the silica membrane filter. Thereafter, 70 (mass/volume)% of an aqueous ethanol solution was permeated through the silica membrane filter to wash the filter, and then purified water was passed to elute the DNA from the silica membrane filter.

For recovering nucleic acids from a human serum sample, specifically, 50 µL of proteinase K and 500 µL of buffer 3 used in Reference Example 2 were added to a human serum sample (500 µL) prepared from 1 mL of a human whole blood sample, followed by mixing to prepare an enzymatic reaction solution. In the same manner as in the recovery of nucleic acids from a human whole blood sample, the resulting enzymatic reaction solution was subjected to an enzymatic reaction, and then a mixture where buffer 4 had been added to the inactivated reaction solution was passed through a silica membrane filter to elute the nucleic acids adsorbed onto the silica membrane filter.

The amount of DNA in the resulting eluate (recovered amount of DNA) and the purity of DNA ([A260]/[A280]) were determined in the same manner as in Reference Example 2. The results are shown in Table 4. As shown in Table 4, the DNA recovery amount recovered from the human whole blood sample was almost comparable to the amount recovered from the human serum sample. Based on these results, it has been suggested that short-chain nucleic acids including desired circulating DNA can be selectively recovered from the whole blood sample according to the nucleic acid recovery method according to the present embodiment, by selectively removing long-chain nucleic acids such as blood cell-derived genomic DNA.

TABLE 4

| Sample name | Recovered amount of DNA (ng) | Purity of DNA (A260/A280) |
|---|---|---|
| Human whole blood sample | 120.0 | 0.7 |
| Human serum sample | 117.5 | 1.0 |

Figure 2:
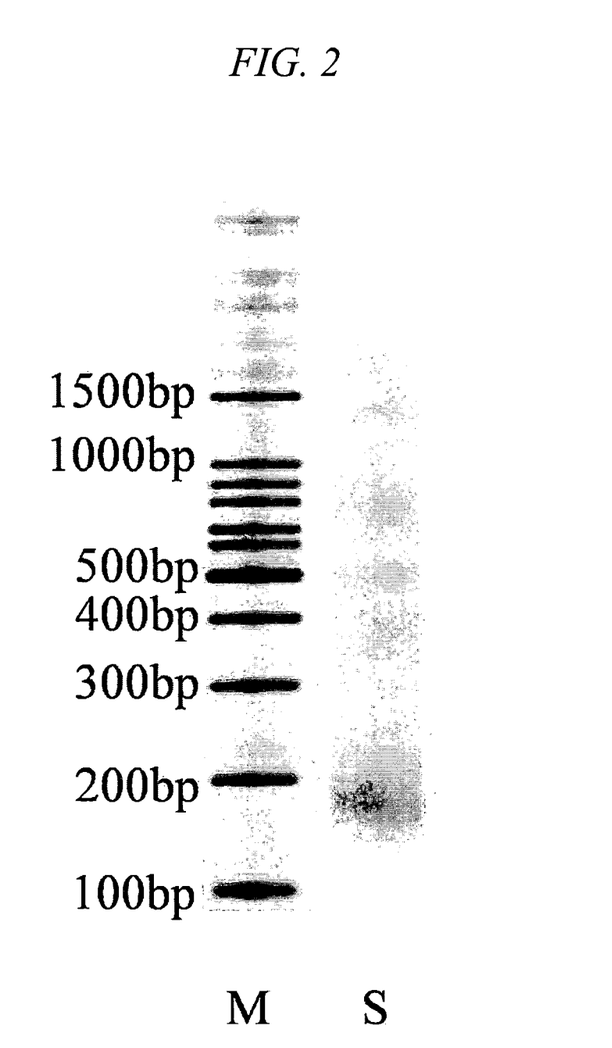
FIG. 2 is a view showing the results of agarose electrophoresis of the recovered eluate in Example 1.

In the same manner as in Reference Example 3, the chain length of DNA obtained from a human whole blood sample by the nucleic acid recovery method according to the present embodiment was confirmed by acrylamide gel electrophoresis. FIG. 2 shows the electrophoresis results. Referring to FIG. 2, the left lane (M) is the electrophoresis results of a 100 bp Ladder DNA marker, and the right lane (S) is the electrophoresis results of the eluate. As shown in FIG. 2, the eluate contained merely fragmented DNA of a short chain length, and particularly a band larger than a 1000 bp marker was not observed at all. Further, fragmentation of DNA could be confirmed from the fact that the band has been smeared.

Based on these results, it has been suggested that short-chain nucleic acids including desired circulating DNA can be selectively recovered from the whole blood sample according to the nucleic acid recovery method according to the present embodiment, by selectively removing long-chain nucleic acids such as blood cell-derived genomic DNA.

Example 2

A short-chain nucleic acid was recovered from a human whole blood sample by the steps (b) and (c) in the nucleic acid recovery method according to a first embodiment of the present invention. That is, in Example 2, a short-chain nucleic acid was recovered by only the steps (b) and (c) in the nucleic acid recovery method according to the present embodiment, and the step (a) was not done.

For recovering nucleic acids from a human whole blood sample, specifically, 50 μL of proteinase K and 500 μL of buffer 3 used in Reference Example 2 were added to 500 μL of a human whole blood sample (the same sample as in Example 1), followed by mixing to prepare an enzymatic reaction solution. In the same manner as in the recovery of nucleic acids from a human whole blood sample, the resulting enzymatic reaction solution was subjected to an enzymatic reaction, and then a mixture where buffer 4 had been added to the inactivated reaction solution was passed through a silica membrane filter to elute the nucleic acids adsorbed onto the silica membrane filter.

The amount of DNA in the resulting eluate (recovered amount of DNA) and the purity of DNA ([A260]/[A280]) were determined in the same manner as in Reference Example 2. The results are shown in Table 5. As shown in Table 5, it can be seen that the DNA recovery amount recovered from the human whole blood sample was significantly higher than the recovered amount of DNA from a human serum sample in Example 1 (Table 4).

TABLE 5

| Sample name | Recovered amount of DNA (ng) | Purity of DNA (A260/A280) |
| --- | --- | --- |
| Human whole blood sample | 1600.0 | 2.1 |

Figure 3:
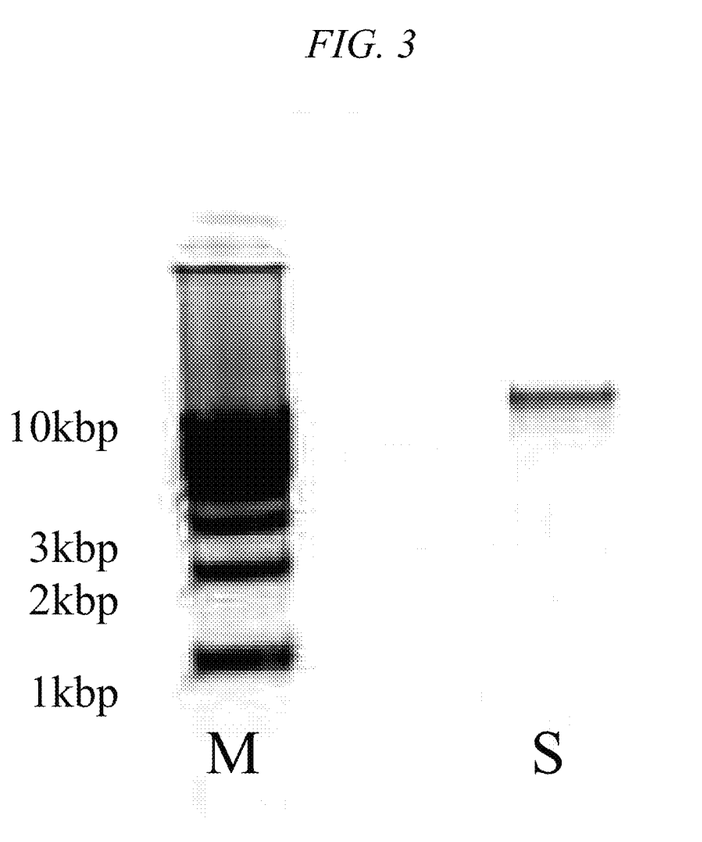
FIG. 3 is a view showing the results of agarose electrophoresis of the recovered eluate in Example 2.

In the same manner as in Reference Example 3, the chain length of DNA obtained from a human whole blood sample was confirmed by agarose gel electrophoresis. FIG. 3 shows the electrophoresis results. Referring to FIG. 3, the left lane (M) is the electrophoresis results of a 1 kbp Ladder DNA marker, and the right lane (S) is the electrophoresis results of the eluate. As shown in FIG. 3, the eluate contained merely DNA of a long chain length, and particularly a band smaller than a 1 kbp marker was not observed at all.

From these results, it is clear that long-chain nucleic acids are preferentially adsorbed and short-chain nucleic acids are not adsorbed in the case where short-chain nucleic acids are recovered by the steps (b) and (c) (without doing the step (a)) in the nucleic acid recovery method according to the present embodiment.

That is, the importance of the treatment previously removing long-chain nucleic acids such as blood cell-derived genomic DNA has been suggested in the step (a) of the nucleic acid recovery method according to the present embodiment.

Example 3

A short-chain nucleic acid was recovered from a human whole blood sample by the nucleic acid recovery method according to a first embodiment of the present invention.

For recovering nucleic acids from a human whole blood sample, specifically DNA was eluted in the same procedure as in Example 1 using buffers 5 and 6 where ethanol was mixed in place of isopropanol in buffers 3 and 4 used in Reference Example 2.

The amount of DNA in the resulting eluate (recovered amount of DNA) and the purity of DNA ([A260]/[A280]) were determined in the same manner as in Reference Example 2. The results are shown in Table 6. As shown in Table 6, it can be seen that the DNA recovery amount recovered from the human whole blood sample was slightly less, as compared to the results of Example 1 using isopropanol (Table 4).

Based on these results, it is clear that short-chain nucleic acids including desired circulating DNA can be selectively recovered from the whole blood sample by selectively removing long-chain nucleic acids such as blood cell-derived genomic DNA, even in the case of using ethanol as a substitute for isopropanol in the nucleic acid recovery method according to the present embodiment. It is clear that the case of using isopropanol is more preferable than the case of using ethanol in the nucleic acid recovery method according to the present embodiment.

TABLE 6

| Sample name | Recovered amount of DNA (ng) | Purity of DNA (A260/A280) |
| --- | --- | --- |
| Human whole blood sample | 103.3 | 0.8 |

Example 4

From a human whole blood sample, a short-chain nucleic acid was recovered without performing an enzymatic treatment (a protease treatment) in the nucleic acid recovery method according to a first embodiment of the present invention.

For recovering nucleic acids from a human whole blood sample, specifically DNA was eluted in the same procedure as in Example 1 using buffers 1 and 2 used in Reference Example 1, except that a protease treatment was not carried out.

The amount of DNA in the resulting eluate (recovered amount of DNA) and the purity of DNA ([A260]/[A280]) were determined in the same manner as in Reference Example 2. The results are shown in Table 7. As shown in Table 7, it can be seen that the DNA recovery amount recovered from the human whole blood sample was less but slightly, as compared to the results of Example 1 (Table 4).

Based on these results, it has been suggested that short-chain nucleic acids including desired circulating DNA can be selectively recovered from the whole blood sample by selectively removing long-chain nucleic acids such as blood cell-derived genomic DNA, even in the case without a protease treatment in the nucleic acid recovery method according to the present embodiment.

TABLE 7

| Sample name | Recovered amount of DNA (ng) | Purity of DNA (A260/A280) |
|---|---|---|
| Human whole blood sample | 99.6 | 0.5 |

What is claimed is:

1. A method of recovering short-chain nucleic acids having a length of 1000 bases or less from a whole blood sample, comprising:
   a step (a) of
      bringing a first mixture into contact with a first nucleic acid adsorbent, the first mixture having an alcohol concentration of 0 to 5 volume %, the first mixture being prepared by mixing a whole blood sample with a first buffer containing at least one selected from a first chaotropic agent and a first surfactant, the first nucleic acid adsorbent to adsorb nucleic acids derived from the whole blood sample onto the first nucleic acid adsorbent, and then
      separating and removing the first nucleic acid adsorbent from being in contact with the first mixture, to recover liquid components of the first mixture;
   a step (b) of
      bringing a second mixture into contact with a second nucleic acid adsorbent, the second mixture having an alcohol concentration of 10 volume % or higher, the second mixture being prepared by mixing the liquid components recovered in the step (a) with a second buffer containing an alcohol, a cationic salt, and at least one selected from a second chaotropic agent and a second surfactant, the second nucleic acid adsorbent to adsorb short-chain nucleic acids having a length of 1000 bases or less, the short-chain nucleic acids derived from the whole blood sample onto the second nucleic acid adsorbent, and then
      separating and recovering the second nucleic acid adsorbent from being in contact with the second mixture including the recovered liquid components; and
   a step (c) of
      eluting the short-chain nucleic acids absorbed in the second nucleic acid adsorbent by bringing water into contact with the second nucleic acid adsorbent recovered in the step (b) and recovering the short-chain nucleic acids from the second nucleic acid adsorbent,
   wherein
      when the first buffer contains the alcohol, the alcohol contained in the first buffer is at least one selected from branched or linear alkanols respectively having 1 to 5 carbon atoms,
      the alcohol contained in the second buffer is at least one selected from branched or linear alkanols respectively having 1 to 5 carbon atoms,
      each agent of the first chaotropic agent contained in the first buffer and the second chaotropic agent contained in the second buffer includes at least one compound selected from the group consisting of a guanidine salt, sodium iodide, and sodium perchlorate,
      each surfactant of the first surfactant contained in the first buffer and the second surfactant contained in the second buffer includes an ionic surfactant including sodium dodecyl sulfate or at least one non-ionic surfactant having a polyoxyethylene group, the at least one non-ionic surfactant selected from the group consisting of polyoxyethylene (10) octylphenyl ether, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (9) octylphenyl ether, polyoxyethylene (23) lauryl ether, polyoxyethylene (20) cetyl ether, digitonin, and saponin, and
      each absorbent of the first nucleic acid adsorbent and the second nucleic acid adsorbent includes at least one selected from the group consisting of a silicic acid-containinq material, zeolite, aluminum oxide, titanium dioxide, zirconium dioxide, kaolin, magnetic particles, ceramics, and polystyrene.

2. The method of recovering short-chain nucleic acids according to claim 1, wherein, in the step (a), a nucleic acid having a length of 5000 bases or more derived from the whole blood sample is to be separated and removed from the first mixture by the first nucleic acid adsorbent adsorbing the nucleic acid having the length of 5000 bases or more onto the first nucleic acid adsorbent.

3. The method of recovering short-chain nucleic acids according to claim 1, wherein
   the first buffer contains guanidine hydrochloride and the first surfactant,
   a concentration of the guanidine hydrochloride in the first buffer is higher than or equal to 1 mol/L and lower than or equal to a maximum solubility of the guanidine hydrochloride in the first buffer, and
   a concentration of the first surfactant is 1 to 10 volume %.

4. The method of recovering short-chain nucleic acids according to claim 1, wherein
   each alcohol of the alcohol in the first mixture when the first mixture includes the alcohol and the alcohol in the second mixture is isopropanol or ethanol, and
   an alcohol concentration in the second mixture of-prepared by mixing the liquid components recovered in the step (a) with the second buffer is 10 to 60 volume %.

5. The method of recovering short-chain nucleic acids according to claim 1, wherein
   each alcohol of the alcohol in the first mixture when the first mixture includes the alcohol and the alcohol in the second mixture is isopropanol, and
   an isopropanol concentration in the second mixture prepared by mixing of-the liquid components recovered in the step (a) with the second buffer is 10 to 40 volume %.

6. The method of recovering short-chain nucleic acids according to claim 1, wherein
   the second buffer contains guanidine thiocyanate as the second chaotropic agent and the second surfactant,
   a concentration of the second chaotropic agent contained in the second buffer is higher than or equal to 0.5 mol/L and lower than or equal to a maximum solubility of the second chaotropic agent in the second buffer, and
   a concentration of the second surfactant contained in the second buffer is 3 to 15 volume %.

7. The method of recovering short-chain nucleic acids according to claim 1, wherein
   a concentration of the cation salt contained in the second buffer is 10 to 200 mmol/L.

8. The method of recovering short-chain nucleic acids according to claim 1, wherein the step (b) further comprises:
a step (b') of adding at least one proteolytic enzyme to the liquid components recovered in the step (a), to carry out an enzymatic reaction, and
a step (b") of
bringing the second mixture into contact with the second nucleic acid adsorbent to adsorb the short-chain nucleic acids having the length of 1000 bases or less, the short-chain nucleic acids derived from the whole blood sample onto the second nucleic acid adsorbent, and then
separating and recovering the second nucleic acid adsorbent from being into contact with the second mixture, after the step (b'),
wherein the at least one proteolytic enzyme includes at least one selected from the group consisting of lysozyme, proteinase, proteinase K, and cellulase.

9. The method of recovering short-chain nucleic acids according to claim 1, wherein the silicic acid-containing material is silica, magnetic silica, glass, or silicon dioxide.

10. The method of recovering short-chain nucleic acids according to claim 1, wherein the short-chain nucleic acids are circulating DNAs.

11. A method of purifying short-chain nucleic acids from a whole blood sample, comprising:
a step (a) of
bringing a first mixture into contact with a first nucleic acid adsorbent, the first mixture having an alcohol concentration of 0 to 5 volume %, the first mixture being prepared by mixing a whole blood sample with a first buffer containing at least one selected from a first chaotropic agent and a first surfactant, the first nucleic acid adsorbent to adsorb nucleic acids derived from the whole blood sample onto the first nucleic acid adsorbent, and then
separating and removing the first nucleic acid adsorbent from being in contact with the first mixture, to recover liquid components of the first mixture;
a step (b) of
bringing a second mixture into contact with a second nucleic acid adsorbent, the second mixture having an alcohol concentration of 10 volume % or higher, the second mixture being prepared by mixing the liquid components recovered in the step (a) with a second buffer containing an alcohol, a cationic salt, and at least one selected from a second chaotropic agent and a second surfactant, the second nucleic acid adsorbent to adsorb short-chain nucleic acids having a length of 1000 bases or less, the short-chain nucleic acids derived from the whole blood sample onto the second nucleic acid adsorbent, and then
separating and recovering the second nucleic acid adsorbent from being in contact with the second mixture including the recovered liquid components; and
a step (c) of
eluting the short-chain nucleic acids absorbed in the second nucleic acid adsorbent by bringing water into contact with the second nucleic acid adsorbent recovered in the step (b) and recovering the short-chain nucleic acids from the second nucleic acid adsorbent, thereby purifying the short-chain nucleic acids from the whole blood sample, wherein
when the first buffer contains the alcohol, the alcohol contained in the first buffer is at least one selected from branched or linear alkanols respectively having 1 to 5 carbon atoms,
the alcohol contained in the second buffer is at least one selected from branched or linear alkanols respectively having 1 to 5 carbon atoms,
each agent of the first chaotropic agent contained in the first buffer and the second chaotropic agent contained in the second buffer includes at least one compound selected from the group consisting of a guanidinium salt, sodium iodide, and sodium perchlorate,
each surfactant of the first surfactant contained in the first buffer and the second surfactant contained in the second buffer includes an ionic surfactant including sodium dodecyl sulfate or at least one non-ionic surfactant having a polyoxyethylene group, the at least one non-ionic surfactant selected from the group consisting of polyoxyethylene (10) octylphenyl ether, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (9) octylphenyl ether, polyoxyethylene (23) lauryl ether, polyoxyethylene (20) cetyl ether, digitonin, and saponin, and
each absorbent of the first nucleic acid adsorbent and the second nucleic acid adsorbent includes at least one selected from the group consisting of a silicic acid-containing material, zeolite, aluminum oxide, titanium dioxide, zirconium dioxide, kaolin, magnetic particles, ceramics, and polystyrene.

12. A kit for recovering short-chain nucleic acids comprising:
a first buffer containing guanidine hydrochloride as a first chaotropic agent and a first surfactant, where
a concentration of the guanidine hydrochloride is higher than or equal to 1 mol/L and lower than or equal to a maximum solubility of the guanidine hydrochloride in the first buffer and
a concentration of the first surfactant in the first buffer is 1 to 10 volume %, the first buffer to be mixed with a whole blood sample to have an alcohol concentration of 5 volume % or lower;
a first nucleic acid adsorbent to
be in contact with the first buffer mixed with the whole blood sample, to adsorb nucleic acids derived from the whole blood sample onto the first nucleic acid adsorbent and
be separated and removed from being in contact with the first buffer mixed with the whole blood sample, so as to recover liquid components of the first buffer mixed with the whole blood sample;
a second buffer containing an alcohol being isopropanol or ethanol, a second chaotropic agent including guanidine thiocyanate, a second surfactant, and a cation salt, the second buffer to be mixed with the liquid components, to have an alcohol concentration of the second buffer being 10 to 60 volume % or higher;
and
a second nucleic acid adsorbent to adsorb short-chain nucleic acids having a length of 1000 bases or less, from the second buffer mixed with the liquid components, wherein
- a concentration of the second chaotropic agent in the second buffer is higher than or equal to 0.5 mol/L and lower than or equal to a maximum solubility of the second chaotropic agent in the second buffer,
- a concentration of the second surfactant in the second buffer is 3 to 15 volume %,
- a concentration of the cation salt in the second buffer is 10 to 200 mmol/L,
- each surfactant of the first surfactant contained in the first buffer and the second surfactant contained in the second buffer includes an ionic surfactant including sodium dodecyl sulfate or at least one non-ionic surfactant having a polyoxyethylene group, the at least one non-ionic surfactant selected from the group consisting of polyoxyethylene (10) octylphenyl ether, polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (9) octylphenyl ether, polyoxyethylene (23) lauryl ether, polyoxyethylene (20) cetyl ether, digitonin, and saponin, and
- each absorbent of the first nucleic acid adsorbent and the second nucleic acid adsorbent includes at least one selected from the group consisting of a silicic acid-containing material, zeolite, aluminum oxide, titanium dioxide, zirconium dioxide, kaolin, magnetic particles, ceramics, and polystyrene.

\* \* \* \* \*